United States Patent
Koltz, Jr. et al.

(10) Patent No.: US 9,664,547 B1
(45) Date of Patent: May 30, 2017

(54) FLOW MANAGEMENT SYSTEM

(71) Applicant: MEDTRONIC XOMED, INC., Jacksonville, FL (US)

(72) Inventors: Michael Lee Koltz, Jr., Jacksonville, FL (US); Mansur Ibne Omar, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

(21) Appl. No.: 14/988,154

(22) Filed: Jan. 5, 2016

(51) Int. Cl.
G01F 1/708 (2006.01)
G01F 1/704 (2006.01)
A61M 3/02 (2006.01)
A61B 17/32 (2006.01)

(52) U.S. Cl.
CPC .............. *G01F 1/704* (2013.01); *A61B 17/32* (2013.01); *A61M 3/0254* (2013.01); *A61B 2217/007* (2013.01); *A61M 2205/3334* (2013.01)

(58) Field of Classification Search
CPC ............ G01F 1/58; G01F 1/708; A61N 1/362
USPC ............................. 73/861.12, 861.05; 600/16
See application file for complete search history.

(56) References Cited

U.S. PATENT DOCUMENTS

| | | | |
|---|---|---|---|
| 8,272,857 B2 | 9/2012 | Norman et al. | |
| 8,882,477 B2* | 11/2014 | Fritz, IV | A61M 1/1015 417/423.12 |
| 8,939,740 B2 | 1/2015 | Norman et al. | |
| 2003/0101826 A1 | 6/2003 | Neubert | |
| 2005/0118048 A1 | 6/2005 | Traxinger | |
| 2006/0020239 A1 | 1/2006 | Geiger et al. | |
| 2009/0013797 A1 | 1/2009 | Heller et al. | |
| 2010/0049119 A1 | 2/2010 | Norman et al. | |
| 2015/0007815 A1* | 1/2015 | Duquette | F04D 25/08 128/202.27 |
| 2015/0139836 A1 | 5/2015 | Norman et al. | |
| 2015/0177035 A1* | 6/2015 | Rovner | G01F 1/584 73/861.12 |

OTHER PUBLICATIONS

International Search Report and Written Opinion of the International Searching Authority, dated Mar. 23, 2017, 13 pages.

* cited by examiner

*Primary Examiner* — Jewel V Thompson
(74) *Attorney, Agent, or Firm* — Dicke, Billig & Czaja, PLLC (57) ABSTRACT

A flow measurement assembly includes a coupler and a flow channel. The coupler maintains a magnet and a sensor spaced from the magnet. The flow channel is positionable between the magnet and the sensor. The flow channel includes a housing having an inlet, an outlet spaced from the inlet, and a flow conduit fluidly open to the inlet and the outlet. A ferrous body is movably disposed in the conduit. The sensor is configured to detect a frequency of a change within a magnetic field as the ferrous body travels within the flow conduit between the magnet and the sensor.

19 Claims, 9 Drawing Sheets

FLOW MANAGEMENT SYSTEM

BACKGROUND

The present disclosure relates to fluid delivery systems. In particular, it relates to fluid delivery systems for medical instruments.

Certain surgical instruments use a supply of fluid for irrigation of a surgical site on a patient as well as for cooling of the surgical instrument. Some non-limiting examples of this type of surgical instrument include micro-debridders, otologic drills, and the like. One common method of providing consistent fluid delivery to a surgical instrument includes pumping fluid from a fluid source, such as a bag, through medical tubing via a positive displacement pump, such as a peristaltic pump. Peristaltic pumps are desirable for many reasons, such as their ability to maintain sterility of the fluid and cleanliness of the pump because the fluid flows through the medical tubing and does not come into contact with components of the pump.

DETAILED DESCRIPTION

Embodiments of the present disclosure are directed to monitoring, or measuring, fluid flow through tubing to a medical appliance, such as a surgical instrument. In general terms, embodiments of the present disclosure can be used to monitor fluid delivery to any medical appliance receiving fluids via medical tubing. Embodiments can detect an empty saline bag, a clamped or occluded irrigation line, a pump failure, or other failures causing irrigation or cooling fluid flow rate to be too high or too low of a desired flow rate. Embodiments of the invention are not limited solely to use with surgical appliances, but can be employed with a wide variety of medical appliances.

A surgical procedure is performed using a surgical instrument including directing an irrigation fluid at a flow rate into the tubing and through the irrigation conduit of the surgical instrument. The irrigation conduit is arranged to direct a fluid stream onto the surgical site and/or to cool a cutting tool of the surgical instrument. A challenge of including flow sensors in a system is to be able to maintain the endotoxins or the pyrogenicity at a level below the industry standards.

Figure 1:
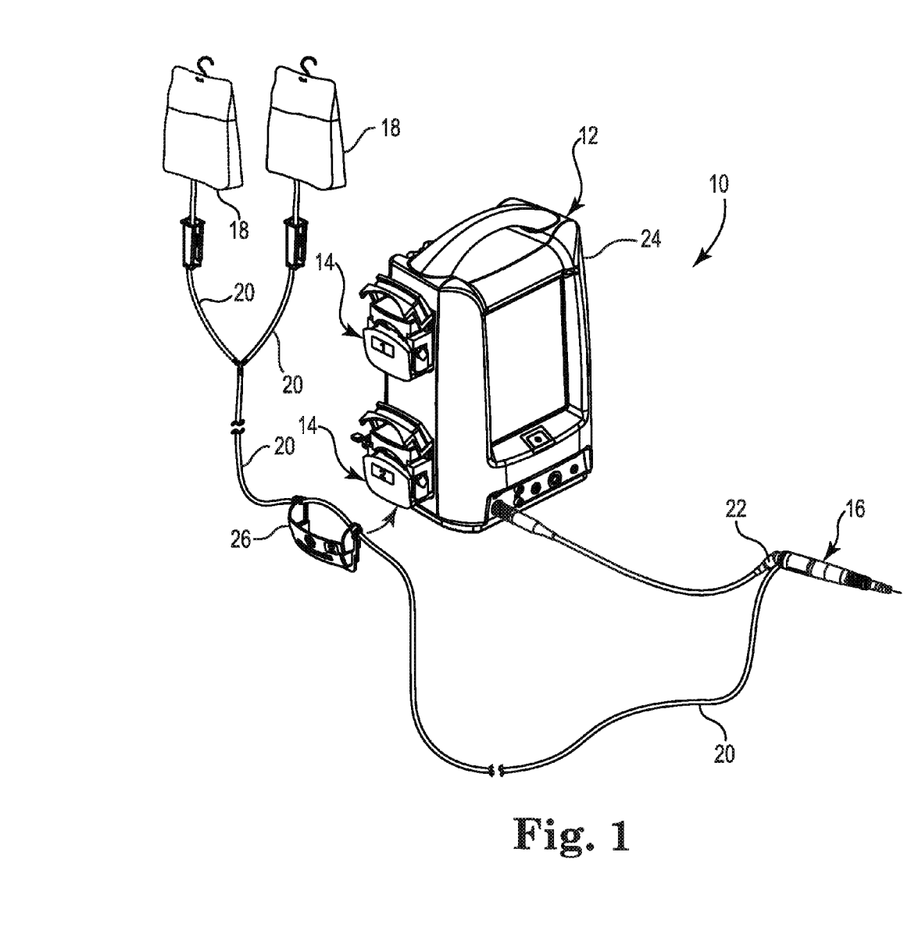
FIG. 1 is a perspective view of a system for delivering and monitoring fluid to a surgical instrument, in accordance with principles of the present disclosure.

A fluid delivery system 10 in accordance with aspects of the present disclosure for supplying fluid to a medical appliance is illustrated in FIG. 1. The system 10 includes a fluid manager 12 (i.e., a console), pump assemblies 14 and a medical appliance 16. Fluid stored in fluid containers 18 is supplied via the respective tubes, or tubing, 20 to pump assemblies 14 to medical appliance 16 as controlled by fluid manager 12. In one aspect, a single tube 20 extends to and is fluidly connected to a proximal end 22 of medical appliance 16. The pump assemblies 14 are mounted onto a housing 24 of the fluid manager 12 and in some embodiments, are releasably secured relative to fluid manager 12 to allow convenient replacement of one or more of pump assemblies 14. In one embodiment, a loading cassette is adapted to facilitate convenient and proper loading of the tube into releasable engagement relative to the peristaltic pumping mechanism of one of the pump assemblies 14.

In general terms, an irrigation pathway is established from containers 18 through tubes 20 and into an irrigation conduit of the medical appliance 16. As described in greater detail below, tube 20 connects to a flow channel of a flow management system of the fluid delivery system 10 adapted to facilitate convenient and proper monitoring of fluid flow through the tubes 20 to the medical appliance 16.

Figure 2:
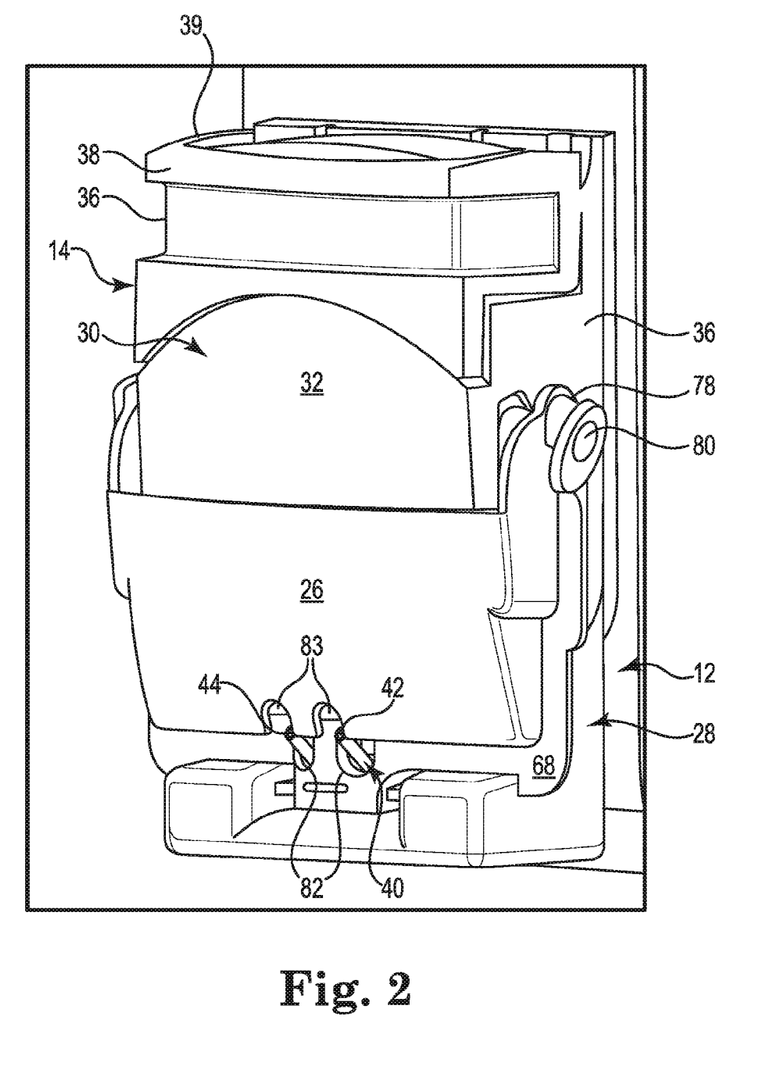
FIG. 2 is a perspective view of a pump assembly and a flow management system coupled to a fluid manager of the system of FIG. 1, in accordance with principles of the present disclosure.

FIG. 2 illustrates a perspective view of the pump assembly 14 coupled to the fluid manager 12. The pump assembly 14 is mounted to the fluid manager 12 via a flow channel coupler 28. The pump assembly 14 in which tubing 20 is to be mounted (via cassette 26) can take many forms. In some embodiments, the pump assembly can take the form of a peristaltic pump assembly 14. As shown in FIG. 2, pump assembly 14 comprises a housing 30 that defines an exterior portion of pump assembly 14 and which includes a front body portion 32, a bottom portion 34 (see, e.g., FIG. 6A), and a pair of opposite side portions 36. A cover mechanism 38 includes a pivotable door 39 that is operable to position a segment of tubing maintained by the loading cassette 26 through pump assembly 14 (see also, e.g., FIG. 1). The loading cassette 26 is assembled into releasable engagement relative to the peristaltic pumping mechanism of the pump assemblies 14. Once a proximal portion of tube is installed in the pump assembly 14 via cassette 26, rollers of the peristaltic mechanism of the pump assembly 14 releasable engage the exterior of the tubing to squeeze or pump the fluid through the tubing 20 in a controlled manner.

The flow channel coupler 28 facilitates mounting of the pump assembly 14 to the fluid manager 12 as well as the flow management system, as described in greater detail below. A flow channel 40 of the flow management system 50 can be assembled to the loading cassette 26 prior to assembly with the pump assembly 14. The loading cassette 26 can be snap fit onto a lower section of the pump assembly 14 and a lower section of the flow channel coupler 28. An inlet connector 42 and an outlet connector 44 of the flow channel 40, each for receiving one end of a piece of surgical tubing, are visible in the pump assembly view of FIG. 2. The inlet connector 42 and the outlet connector 44 of the flow channel 40 project outward from the front body portion 32 loading cassette 26 for assembly with tubing. The fluid moved through the tubing by the pump assembly 14 is pushed to the flow channel 40 and a rate of fluid flow is sensed and measured by the flow management system as the fluid flow through the flow channel as described in greater detail below.

Figure 3:
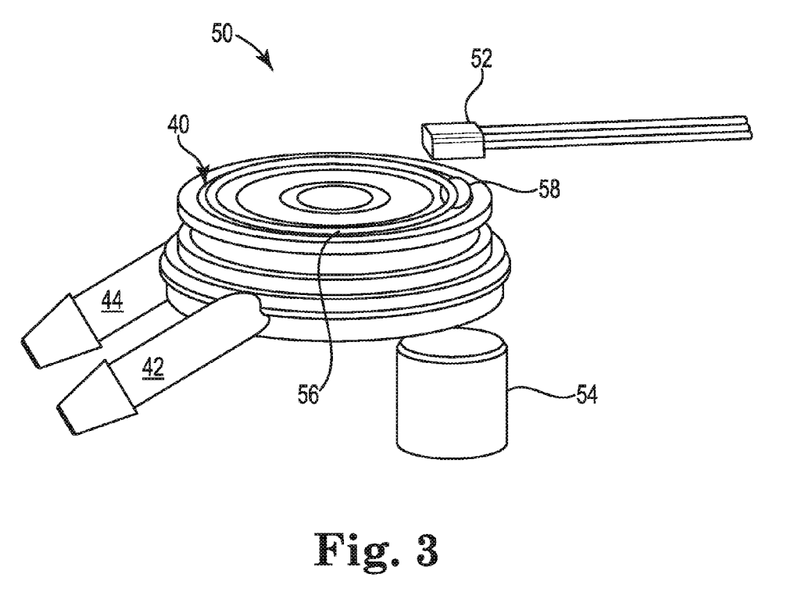
FIG. 3 is a schematic illustration of a flow management system in accordance with principles of the present disclosure.

With the above general construction of system 10 in mind, FIG. 3 is a schematic illustration of a flow management system 50 useful in the fluid delivery system 10. In general terms, the flow management system 50 includes a sensor 52 and a magnet 54, with the flow channel 40 positionable between the sensor 52 and the magnet 54. The flow channel 40 can be in many different forms. The flow channel 40 includes the inlet connector 42 and the outlet connector 44 fluidly open to a flow conduit, or track 56.

The flow channel 40 includes a ferrous body 58 movable within the flow conduit, or track, 56 of the flow channel 40. The track 56 can be circular or toroidal, with the ferrous body 58 movable in an oscillatory fashion around the circular or toroidal track 56 of the flow channel 40. The track 56 of the flow channel 40 is positioned between the magnet 54 and the sensor 52 such that the ferrous body 58 passes between the magnet 54 and the sensor 52 as the ferrous body 58 travels along the track 56. A spacing of the magnet 54, the sensor 52, and the ferrous body 58 is maintained to provide sufficient magnet field to influence the sensor 52 and provide to an air gap between the magnet 54 and the sensor 52. The ferrous body 58 is magnetically attracted to the magnet 54. A fixed distance between the magnet 54 and the ferrous body 58 provides a static magnetic field that allows the ferrous body 58 to move through the static magnetic field.

To move the ferrous body 58, fluid flows into the inlet connector 42, through the flow conduit 56, and exits at the outlet connector 44. FIG. 6D is a cross-sectional view of the pump assembly at a parallel plane disposed adjacent to the cross-section illustrated in FIG. 6A. As illustrated in FIG. 6D, a nozzle 59 extends through the inlet connector 42 to the track 56 of the flow channel 40 tapering to an inwardly reduced cross-section and the flow area is reduced as the fluid enters through the inlet connector 42. The nozzle 59 increases the hydraulic power and kinetic energy of the fluid moving through the flow channel 40. The increased kinetic energy accelerates the movement of the ferrous body 58 traveling through the track 56 and to offset the effect of the kinetic energy losses resulting from drag, surface tension, and magnetic attraction forces, for example, as the ferrous body 58 travels through the track 56.

Figure 4A:
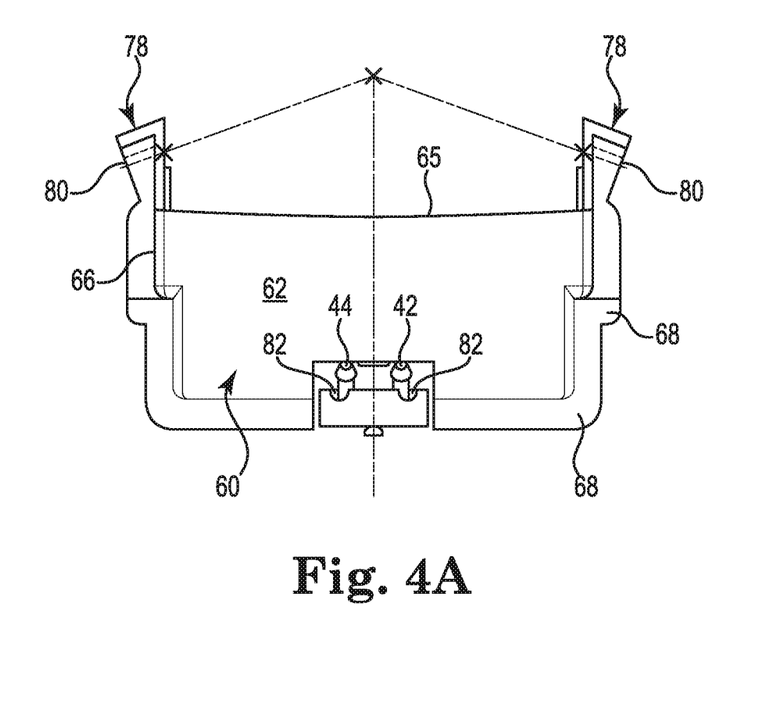
FIGS. 4A-4B are perspective views of a flow channel coupler in accordance with principles of the present disclosure.
Figure 4B:
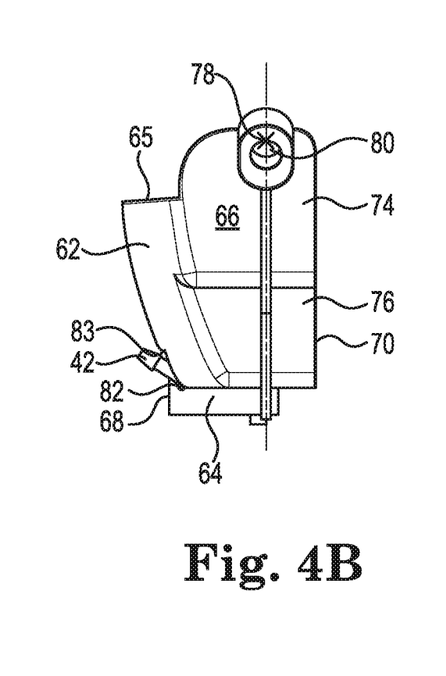

FIGS. 4A and 4B illustrate front and side views of the loading cassette 26 for assembling the flow channel 40 to the fluid manager 12 at a pump assembly (e.g., pump assemblies 14). The flow channel 40 can be pre-assembled with the loading cassette 26 prior to mounting with the pump assembly 14 and flow channel coupler 28. In one embodiment, the loading cassette 26 and the flow channel 40 are disposable after use in system 10.

In general terms, the cassette 26 can assume a variety of forms and is sized and shaped to slidably fit over and remain engaged with one of the pump assemblies 14 (FIGS. 1 and 2) to position a segment of tubing for engagement with interior components of the respective pump assemblies 14. In general terms, loading cassette 26 comprises a shell 60 forming a recess or pocket that is sized and shaped to slidably fit over and securely engage an exterior housing of a pump assembly. In one embodiment, the shell 60 of the loading cassette 26 is defined by a front wall 62, a bottom wall 64, a top edge 65, and side walls 66. In addition, in some embodiments, a flange 68 extends outwardly from the bottom wall 64 and the side walls 66 of the shell 60. In another aspect, the side walls 66 include a rear edge 70 and the bottom wall 64 includes a rear edge 72. In some embodiments, each side wall 66 of shell 60 includes an upper portion 74 and a lower portion 76 with the upper portion 74 extending vertically upward relative to the top edge 65 of shell 60. The loading cassette 26 further includes a pair of guides 78 extending outwardly from the upper portion 74 of the respective side walls 66 of shell 60. Each guide 78 defines a hollow elongate sleeve 80 extending between an inner end and an outer end. The elongate sleeve 80 defined by each guide 78 forms an acute angle relative to the respective side walls 66 of cassette 26. The angle of the sleeve 80 is selected to cause any tubing extending through the guide 78 to extend vertically upwardly at an angle for entry within a roller-tube engagement zone of the pump assembly 14.

The flow channel 40 is mechanically coupled to the loading cassette 26 along the front and bottom walls 62, 64 of the loading cassette 26. Flow channel 40 can be horizontally centered within the loading cassette 26 along the front wall 62 or otherwise positioned to cooperate and align with the magnet 54 and the sensor 52 housed in the flow channel coupler 28. The loading cassette 26 includes ports 82 on the front wall 62 that the inlet and outlet connectors 42, 44 are extendable through. The front wall 62 of the shell 60 can also include indentations or recesses 83 above the ports 82 to provide sufficient access to the inlet 42 and outlet 44 for connection to tubing. The inlet and outlet connectors 42, 44 can be angled upward primarily to facilitate venting of air during priming operation to the tubing along the front wall 62 of the cassette 26. In one embodiment, the inlet and outlet connectors 42, 44 are disposed at an angle of 30 degrees upward from a horizontal plane. Other angles may also be acceptable.

Figure 5A:
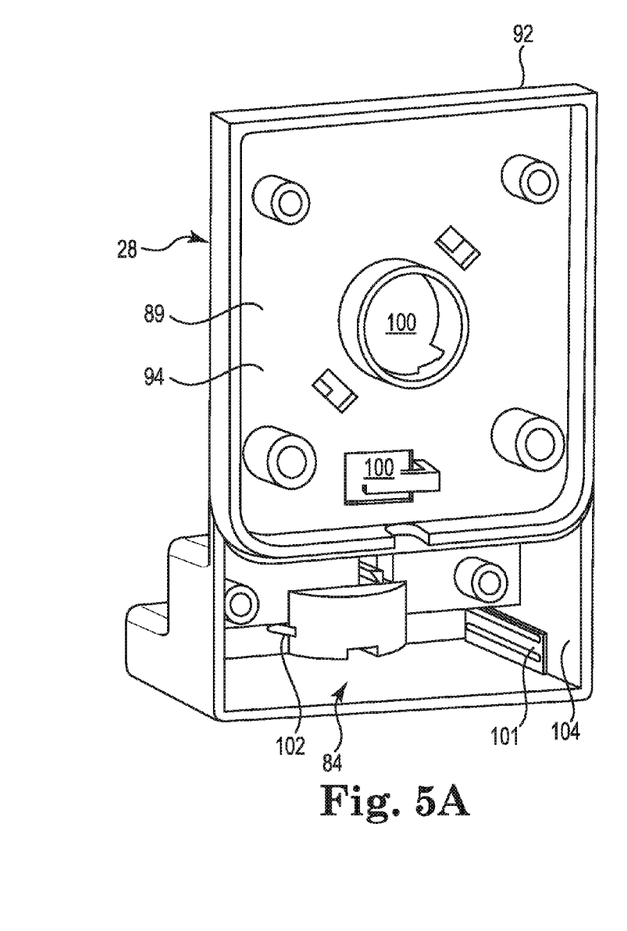
FIGS. 5A-5B are front and side views of a loading cassette in accordance with principles of the present disclosure.
Figure 5B:
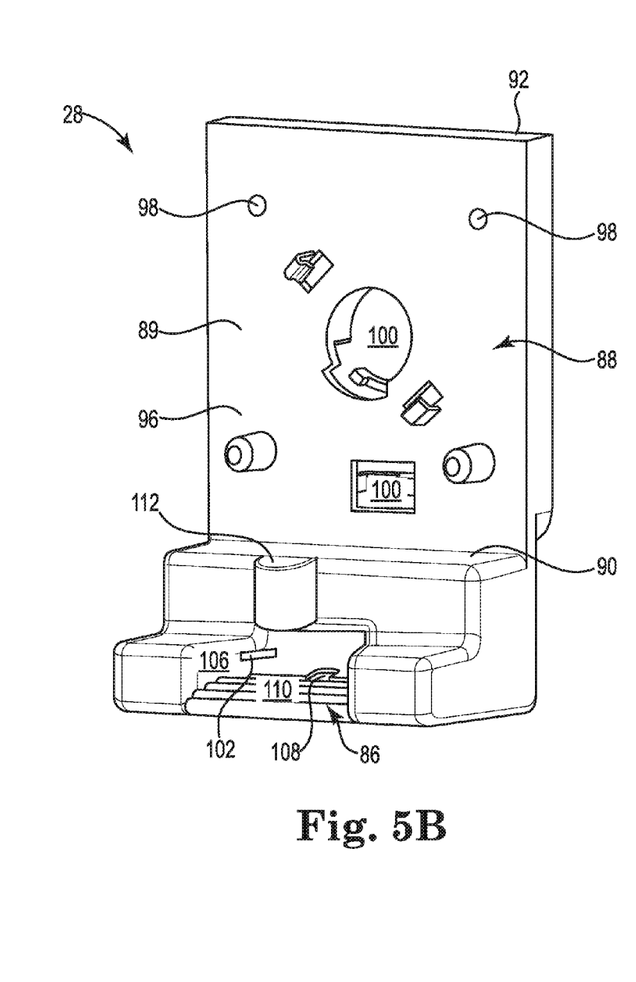

FIGS. 5A and 5B illustrate front and back perspective views of a flow channel coupler 28. The flow channel coupler 28 includes a circuit board cavity 84, a flow channel cavity 86, or recess, and a pump section 88. Flow channel coupler 28 can have a tiered, or stepped, shape to define the respective cavities. The pump section 88 includes a back portion 89 and a lower portion 90. The back portion 89 extends from a top 92 of the flow channel coupler 28 to the lower portion 90 and has a height similar to a height of the pump assembly 14 and is configured to couple to a side of the fluid manager 12 suitable for coupling of the pump assembly 14. With additional reference to FIG. 6A, the pump assembly 14 is mounted to the fluid manager 12 through the upper/back portion 89 of the flow channel coupler 28. The pump assembly 14 is positioned against the lower and back portions 89, 90 of the flow channel coupler 28. The back portion 89 has a back 94 and a front 96 and can provide structural stability and strength without adding substantially to the overall side profile thickness of the pump assembly attachment to the fluid manager 12. The back portion 89 includes fastener attachment openings 98 to facilitate coupling of the pump 14 to the fluid manager 12 through the flow channel coupler 28. The back portion 89 also includes openings 100 to facilitate mechanical, electrical, and control connections (e.g., drive motor) of the pump assembly 14 to the fluid manager 12. In one embodiment, the flow channel coupler 28 is formed of a molded plastic.

The circuit board cavity 84 is open at the back 94 for receiving a circuit board (see, e.g., FIGS. 6A-6C) and extends under the flow channel cavity 86. The circuit board cavity 84 can include opposing slots 102 on interior side wall 104 of the circuit board cavity 84 for inserting and slidably retaining a circuit board in the flow channel coupler 28 under the flow channel 40. The flow channel cavity 86 is separated from the circuit board cavity 84 by cavity walls 106. A sensor opening 108 can be provided in a bottom wall 110 of the flow channel cavity 86. The flow channel recess 86 is open at the front for removable insertion of the flow channel. The flow channel cavity 86 is sized and shaped to securely position the flow channel 40. A magnet recess 112 is positioned above the flow channel recess 86.

Figure 6A:
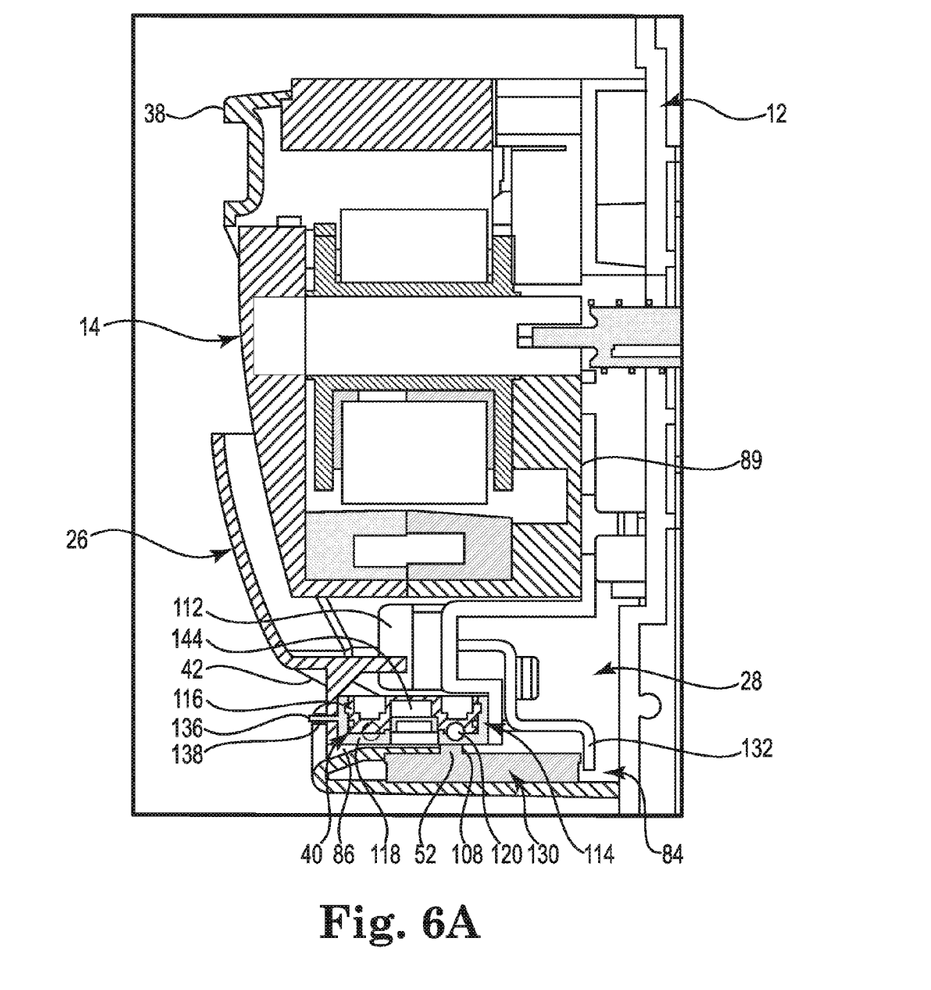
FIG. 6A is a cross-sectional view of the pump assembly of FIG. 2, in accordance with principles of the present disclosure.
Figure 6B:
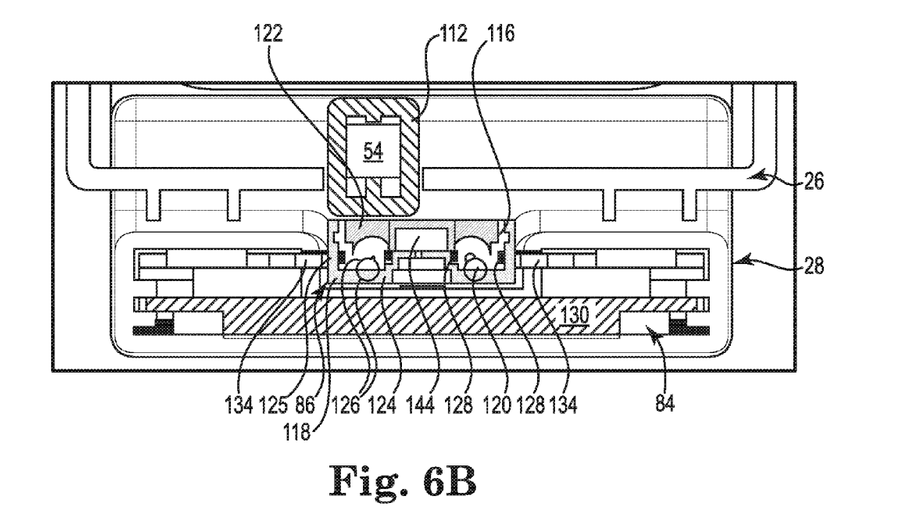
FIGS. 6B-6D are exploded partial cross-sectional views of the pump assembly of FIG. 2, in accordance with principles of the present disclosure.
Figure 6C:
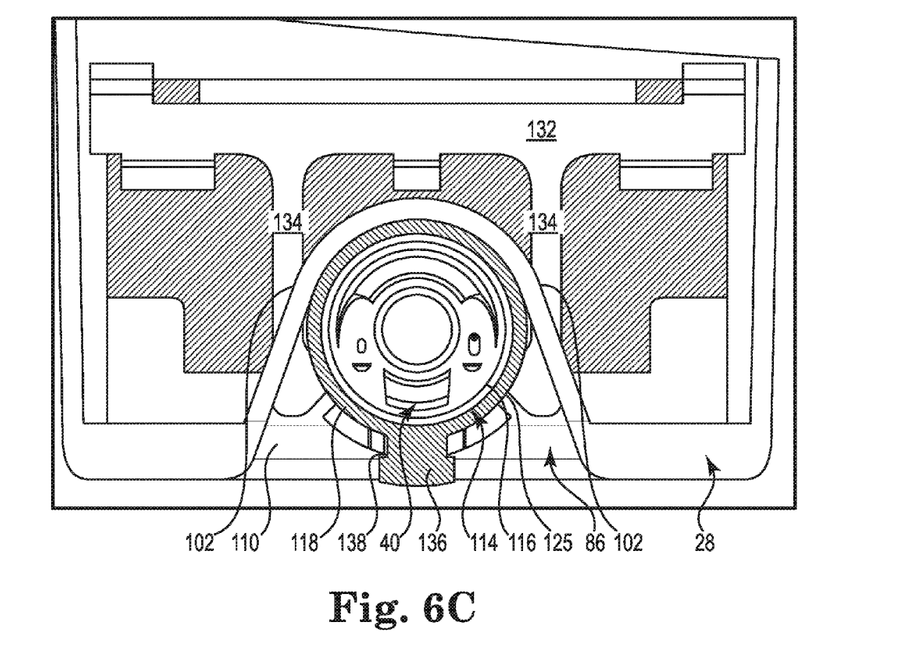
Figure 6D:
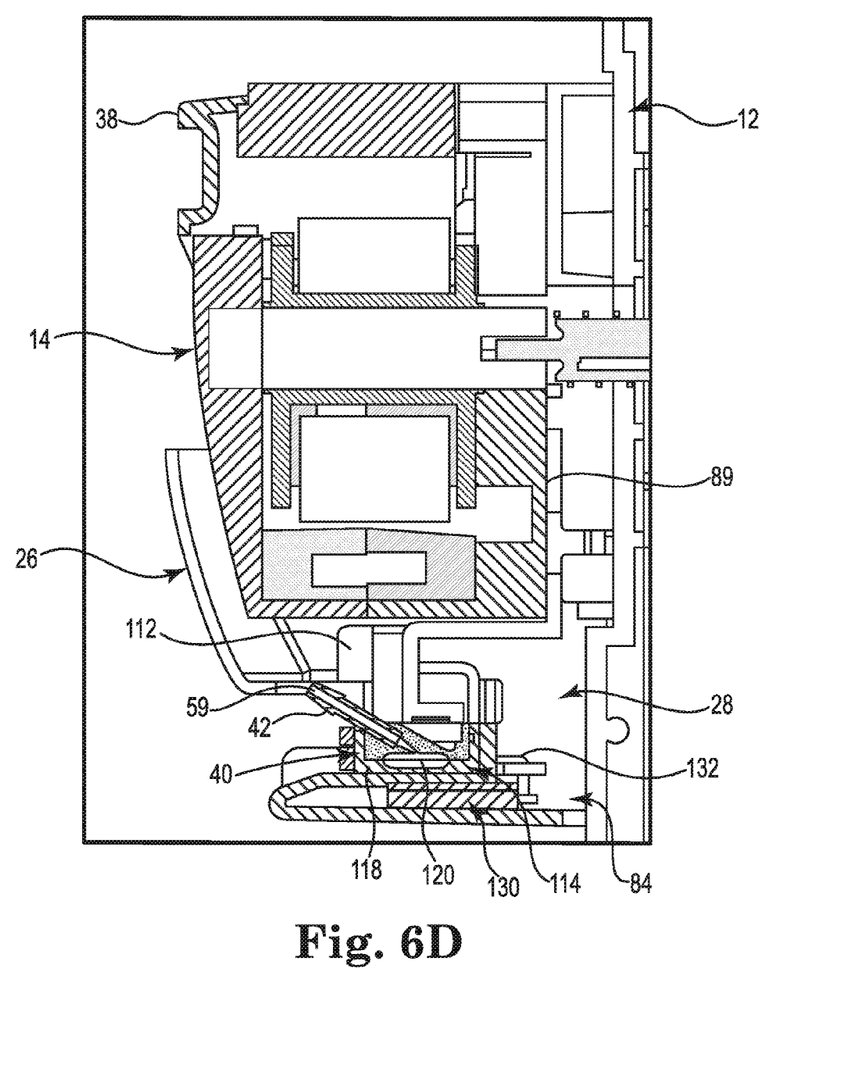

With additional reference to the cross-sectional illustrations of FIGS. 6A-6C, a housing 114 of the flow channel 40 can be formed of a first portion 116 and a second portion 118. The first and second portions 116, 118 can be assembled together to form a flow track, or conduit, 120. In one embodiment, the first and second portions 116, 118 snap fit together. The inlet and outlet connectors 42, 44 extend from the housing 114, in one embodiment, from the first portion 116, at an obtuse angle from a top surface 122. The second section 118 forms a bottom surface 124 and outer side surface 125 of the flow channel 40. The first and second portions 116, 118 include internal recesses 126 that fluidly join to form the track 120. In one embodiment, the recesses 126 are semi-circular. The flow housing 114 can be formed of a molded hard plastic such as polyvinylchloride, for example. The housing can include a transparent first section 116 in order that the flow conduit, or track 120, is visible. A seal 128, such as an o-ring, provides a fluid seal upon assembly of the first and second portions 116, 118. The seal 128 can also be a solvent weld or ultrasonic weld. The seal 128 prevents the flow from bypassing the flow conduit or track 120 and helps keep the fluid flow contained in the housing 114. In one embodiment, there are two seals 128 with one seal 128 positioned inner side the track 120 and the second seal 128 positioned outer side of the track 120. The ferrous body 58 is disposed in the flow track 120 formed by semi-circular recesses 126 in the first and second portions 116, 118. The ferrous body 58 can be spherical, i.e., in the shape of a ball. In one embodiment, the ferrous body 58 is a 440C stainless steel ball.

The magnet 54 and a circuit board 130 are housed in the flow channel coupler 28 that is mounted to the surgical instrument console 12. The circuit board 130 is secured within the circuit board cavity 84 with a retaining clip 132 extending along a back edge of the circuit board 130. The retaining clip 132 can also extend above the circuit board 130 and include arms 134 to removably secure the flow channel 40 in the flow channel recess 86. The arms 134 can act as a spring clip. Ends of arms 134 extend through openings 102 in sidewalls 106 of the flow channel recess 86. The circuit board 130 includes the sensor 52 and signal processing circuitry. The magnet 54 is housed in the magnet recess 112 positioned above the flow channel cavity 86. In one embodiment, the magnet 54 is insertable from top or bottom into recess 112. The magnet 54 can be a permanent magnet or an electromagnet, for example. The magnet 54 has a north pole and a south pole that are oriented with respect to the ferrous body 58 and the sensor 52.

When the flow channel 40 is inserted and coupled to the flow channel coupler 28, the flow channel 40 is positioned between the magnet 54 and the sensor 52. In one example, the flow channel 40 includes a coupling leg 136 insertable into a slot 138 in the front wall 64 of the loading cassette 26. The coupling leg 136 can include a protruded end for selectively releasable extension through and engagement with slot 138. The flow channel coupler 28 maintains a spacing of the magnet 54, the sensor 52, and the ferrous body 58 disposed in the flow channel 40 to provide a sufficient magnet field to influence the sensor 52 and provide an air gap between the magnet 54 and the sensor 52 (see also, e.g., FIG. 3). The ferrous body 58 is magnetically attracted to the magnet 54. The fixed distance between the magnet 54 and the ferrous body 58 provides a static magnetic field that allow as the ferrous body 58 to move through the static magnetic field. The sensor 52 senses magnetic field interruptions or disturbances as the ferrous body 58 moves through the static magnetic field created by the magnet 54.

Figure 7:
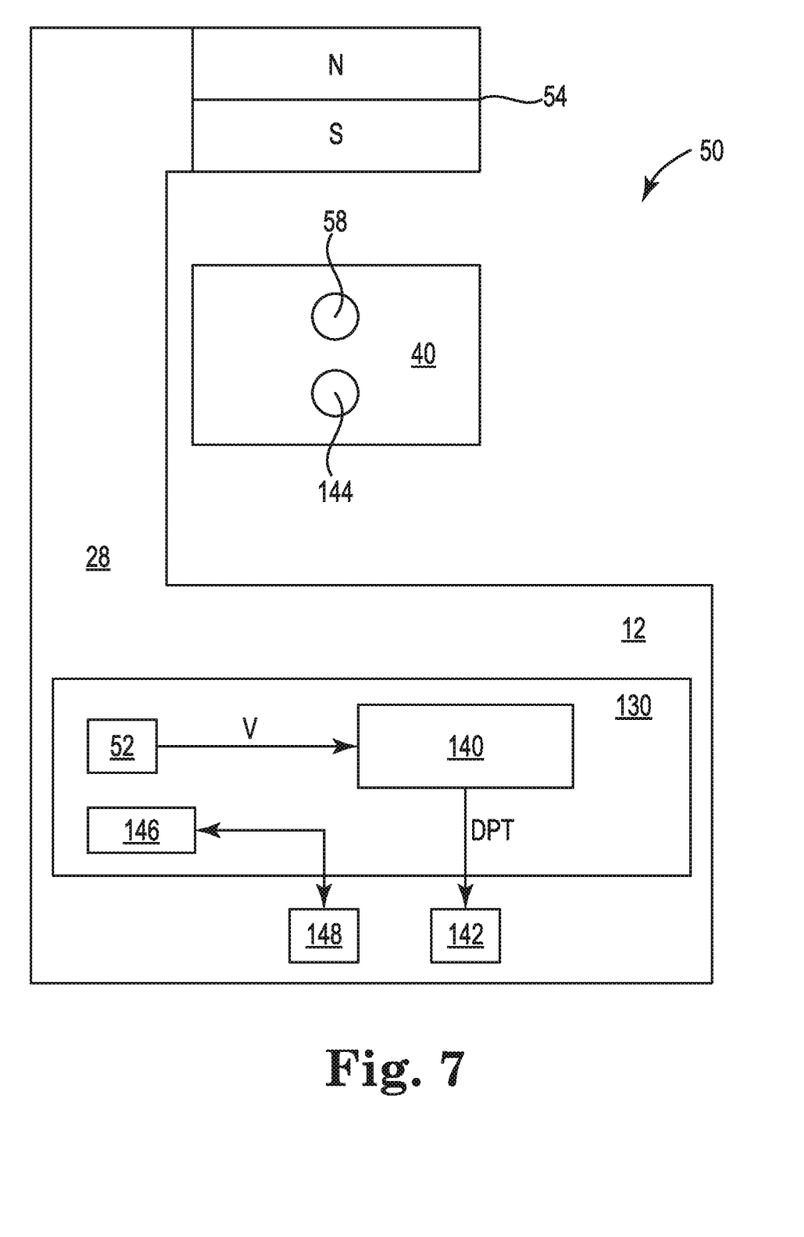
FIG. 7 is a block diagram of the flow management system in accordance with principles of the present disclosure.

With reference to the block diagram of FIG. 7, the system 50 includes the sensor 52 positioned on the circuit board 130 along with signal processing circuitry 140. In one embodiment, the sensor 52 is a hall sensor capable of measuring the magnetic field directly. The sensor 52 senses changes in the magnetic field. The magnetic field changes as the ferrous body 58 travels past the magnet 54 and the sensor 52 senses the resultant magnetic field changes. The sensor 52 picks out the variation in the magnetic field and converts it into voltage, as indicated by arrow "V". The change in the magnetic field which is, in turn, a frequency that is proportional to the flow rate because the fluid flow is moving the ferrous body 58 through the track 56. The static field in proximity to the ferrous body 58 is disturbed as the ferrous body 58 passes by the magnet 54. The disturbance is detected by the sensor 52, such as a Hall sensor. The sensor 52 converts the magnetic field change into a frequency. Additional signal conditioning, or signal processing, is performed by the sensor 52 to filter and amplify the frequency. In one embodiment, the output frequency is proportionate to the flow rate. The signal processing circuitry 140 takes the output of the sensor 52 and converts it for a digital signal processor 142. The circuitry 140 filters, amplifies and digitizes the signal. The console 12 can be programmed to convert the frequency to a flow rate. The console 12 can be programmed with predetermined flow rates to identify operation of the surgical instrument. In one embodiment, a target flow rate is between 20-60 cubic centimeters per minute (cc/min). For example, a flow rate that is determined to be insufficient to provide proper irrigation flow to a surgical cutter can signal the console to notify a user or to stop rotation of the cutter. For example, insufficient flow may be due to a user forgetting to unclamp the irrigation line when setting up the surgical system. Notification of insufficient flow can prompt a user to check the irrigation line.

As described above, the flow management system 50 measures the flow rate of a fluid (i.e., liquid or gas). The active sensing body 52 and the magnet 54 are assembled outside of the flow channel 40, within non-disposable flow channel coupler 28. The ferrous body 58 is assembled inside the conduit track 56 of the flow channel 40. The flow channel 40 can be disposable. The separation and disposability of the flow channel 40 from the electronic circuit board 130 and the magnet 54 allows the electronic circuit board 130 and the magnet 54 to remain isolated from the fluid flow, such as saline, allowing biocompatibility and endotoxin reduction and increased reliability of the electronics.

The system 50 measures the flow rate by measuring the frequency of change within a magnetic field as the ferrous body 58 (such as a ball) moves within the conduit 56 between the static permanent magnet 54 and the sensor 52. The ferrous body 58 is moved when the fluid flows within the conduit 56. The sensor 52 produces an analog output voltage waveform that is periodic within a flow rate range. Front end analog signal conditioning circuit 140 filters and amplifies the analog voltage signal within a predetermined frequency range and then the amplified signal is then converted into a digital signal pulse train, as indicated by arrow "DPT".

The presence of the flow channel 40 assembled to the flow channel coupler 28 can be detected using a radio frequency identification (RFID). The flow channel 40 can include a radiofrequency (RF) tag 144 and a RF antennae 146 can be included in the flow channel coupler 28 in the circuit board 130 or elsewhere in the pump assembly or fluid manager. When the flow channel 40 is inserted with the cassette 26 into the fluid manager 12, the fluid manager 12 recognizes that a cassette 26 has been inserted and there is a flow channel 40 ready to measure fluid flow. The RFID can also aid in tracking the use of the disposable flow channels 40. The system 10 detects the presence of the flow channel 40 by reading the pre-stored identification data from the RFID tag 144 embedded on or near the flow channel 40. A RF antenna 146 is placed proximate to the RFID tag 144 which is interfaced with an RFID reader 148. The RFID reader 148 reads the RFID tag 144 information to determine the presence of the flow channel 40. The front end analog signal conditioning circuit 140 and the RF antenna 146 are integrated in the printed circuit board 130 located proximate to the flow channel 40. The RF antenna 146 is interfaced with an RFID reader module 148, and the output of the analog signal conditioning circuit 140 is interfaced with the host system, such as fluid manager 12.

The RFID reader module 148 is interfaced with the fluid manager 12 over a serial data communication channel (e.g., RS 232). When commanded by the fluid manager 12, the RFID reader 148 reads the pre-defined content of the RFID tag 144 by delivering RF energy to the RFID tag 144 via the RF antenna 146. The fluid manager 12 receives the digital pulse train "DPT" from the signal conditioning circuit 140 and calculates the frequency of the signal via digital signal processor (DSP) 142. The frequency of the digital signal pulse train "DPT" is proportional to the flow rate through the flow channel 40.

Although the present disclosure has been described with reference to preferred embodiments, workers skilled in the art will recognize that changes can be made in form and detail without departing from the spirit and scope of the present disclosure.

What is claimed is:

1. A flow measurement assembly, comprising:
    a coupler maintaining a magnet and a sensor spaced from the magnet; and
    a flow channel positionable between the magnet and the sensor, the flow channel comprising:
        a housing having an inlet, an outlet spaced from the inlet, and a flow conduit fluidly open to the inlet and the outlet; and
        a ferrous body movably disposed in the conduit,
    wherein the sensor is configured to detect a frequency of a change within a magnetic field as the ferrous body travels within the flow conduit between the magnet and the sensor.

2. The flow measurement assembly of claim 1, further comprising electronic circuitry.

3. The flow measurement assembly of claim 1, further comprising a radiofrequency identification tag on the flow channel.

4. The flow measurement assembly of claim 1, wherein the magnet is a permanent magnet.

5. The flow measurement assembly of claim 1, wherein the housing includes a first portion coupled to a second portion and the conduit is formed between the first portion and second portion.

6. The flow measurement assembly of claim 1, wherein the inlet has a smaller cross-sectional area than the outlet.

7. The flow measurement assembly of claim 1, wherein the conduit is circular.

8. A flow measurement system, comprising:
    a fluid source;
    a tubing set including a first tube and a second tube, the first tube fluidly connected to the fluid source;
    a power console including a pump for moving fluid from the fluid source to a medical device;
    a flow channel coupler attached to the power console at the pump, the flow channel coupler including a magnet and a circuit board having a sensor spaced from the magnet;
    a loading cassette including a tube segment attachable into the pump, the tube segment including in the first tube; and
    a flow channel assembled with the pump cassette, the flow channel disposed between the magnet and the sensor when assembled with the pump, the flow channel including an inlet, an outlet, and a flow conduit fluidly open to the inlet and the outlet, a ferrous body movably disposed in the conduit, the first tube coupled to the inlet and the second tube coupled to the outlet,
    wherein a fluid flow rate through the flow channel to the medical device is measured by the sensor detecting a frequency of a change within a magnetic field as the ferrous body travels with a fluid flow within the conduit between the magnet and the sensor.

9. The flow measurement system of claim 8, wherein the loading cassette and the flow channel are disposable.

10. The flow measurement system of claim 8, wherein the printed circuit board includes a radiofrequency antenna and the flow channel includes a radiofrequency identification tag.

11. The flow measurement system of claim 8, wherein the circuit board and the magnet are fluidly separated from the fluid flow.

12. The flow measurement system of claim 8, wherein the medical device is coupled to the power console at a connector panel and coupled to the second tube, wherein the fluid flows to the medical device and exits the device.

13. The flow measurement system of claim 12, wherein the medical device is a surgical cutting instrument having a cutting tip and the fluid exits adjacent the cutting tip.

14. The flow measurement system of claim 8, wherein the inlet has a small interior cross-sectional area than the first tube.

15. A method of measuring fluid flow to a surgical instrument, comprising:
    assembling a flow channel with a pump;
    positioning the flow channel between a magnet and a sensor;
    detecting a flow channel assembled to a pump in an irrigated medical device assembly;
    connecting a fluid source to an inlet of the flow channel;
    connecting a medical device to an outlet of the flow channel;
    pumping fluid from the fluid source through the flow channel including a fluid conduit disposed between the inlet and outlet;
    moving a ferrous body within the fluid conduit with the flow of the fluid;
    pushing the ferrous body repeatedly between a magnet and a sensor at a velocity associated with the flow of fluid through the conduit;
    sensing a change within a magnetic field as the ferrous body moves within the conduit between the magnet and the sensor; and
    determining a flow rate from the sensed change within the magnetic field.

16. The method of claim 15, wherein the fluid is fluidly separated from the magnet and the sensor.

17. The method of claim 15, wherein detecting the flow channel assembled to the pump is with radiofrequency identification.

18. The method of claim 15, further comprising:
- amplifying the analog voltage signal within a predetermined frequency band; and
- converting the amplified signal to a digital signal pulse train.

19. The method of claim 15, producing an analog output voltage waveform associated with a flow rate of the fluid through the conduit;
- processing a frequency of the analog voltage signal with a digital signal processor; and
- correlating the frequency with a proportionally associated flow rate.

* * * * *